(12) United States Patent
Hurry et al.

(10) Patent No.: US 7,138,367 B2
(45) Date of Patent: Nov. 21, 2006

(54) GEL COMPOSITIONS FOR DIFFUSION DEVICES

(75) Inventors: Simon Hurry, Ascot (GB); Stephen Barnes, High Wycombe (GB); Nicholas O'Leary, Slough (GB)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/901,066

(22) Filed: Jul. 29, 2004

(65) Prior Publication Data

US 2004/0262421 A1    Dec. 30, 2004

Related U.S. Application Data

(63) Continuation of application No. PCT/IB03/00950, filed on Mar. 4, 2003.

(30) Foreign Application Priority Data

Mar. 13, 2002  (WO) ........................ PCT/IB02/00767

(51) Int. Cl.
    *A61L 9/04*    (2006.01)
(52) U.S. Cl. .............................. 512/4; 239/34; 239/60; 424/76.3; 424/76.4; 424/76.8
(58) Field of Classification Search .................... 512/4; 239/34, 60; 424/76.4, 76.8, 76.3
    See application file for complete search history.

(56) References Cited

U.S. PATENT DOCUMENTS 3,969,280 A * 7/1976 Sayce et al. .................. 512/4

| | | | |
|---|---|---|---|
| 5,556,835 A | 9/1996 | Inaoka et al. | 512/3 |
| 5,635,171 A * | 6/1997 | Nadaud | 424/78.03 |
| 6,435,423 B1 * | 8/2002 | Hurry et al. | 239/34 |
| 2001/0030243 A1 | 10/2001 | Hurry et al. | 239/60 |

FOREIGN PATENT DOCUMENTS

| | | |
|---|---|---|
| EP | 0 631 788 A1 | 1/1995 |
| EP | 0 835 666 A2 | 4/1998 |
| EP | 0 904 771 B1 | 3/1999 |
| EP | 0 934 343 B1 | 8/1999 |
| FR | 2 803 746 | 7/2001 |
| WO | WO 98/18828 | 5/1998 |
| WO | WO 98/19717 | 5/1998 |
| WO | WO 00/24435 | 5/2000 |

* cited by examiner

*Primary Examiner*—Monique T. Cole
(74) *Attorney, Agent, or Firm*—Winston & Strawn LLP

(57) ABSTRACT

The invention concerns a gel composition capable of bringing a benefit or effect by diffusing into its surrounding environment an active volatile. The compositions according to the invention include a water based medium, comprising an active volatile, a super-absorbent polyacrylate based polymer and a polymeric cross-linking agent having a high molecular weight and being able to be polarized with positive charges. The invention also concerns the consumer article containing, or associated with, the composition, in particular a device intended to diffuse a volatile liquid, more specifically an air-freshener.

19 Claims, 1 Drawing Sheet

GEL COMPOSITIONS FOR DIFFUSION DEVICES

CROSS-REFERENCE TO RELATED APPLICATION

This application is a continuation of International application PCT/IB03/00950 filed Mar. 4, 2003, the entire content of which is expressly incorporated herein by reference thereto.

TECHNICAL FIELD

The invention concerns a gel composition capable of bringing a benefit or effect into its surrounding environment by diffusing an active volatile.

The compositions according to the invention comprise:
a) a water based medium, comprising an active volatile;
b) a super-absorbent polyacrylate based polymer; and
c) a polymeric cross-linking agent having a high molecular weight and being able to be polarized with positive charges.

The invention also concerns the consumer article containing, or associated with, the composition, in particular a device intended to diffuse an active volatile, more specifically an air-freshener.

BACKGROUND ART

It is known that gel compositions for dispersing volatile material may be prepared from many different polymeric resins.

Among these gels, those that are based on super-absorbent polyacrylate polymers are of particular interest and are described in WO 00/24435 or in EP 835666. The super-absorbent gels have the advantage of requiring small quantities of resin and providing an effective release of the active ingredient for a prolonged period of time.

However, the disclosed gels based on the super-absorbent polyacrylate polymers suffer from the disadvantage of having poor mechanical properties. The consequence of which is that the gels can be easily deformed or broken, under a slight mechanical pressure or a slump, with the undesired consequence that the releasing behaviors are altered, by the change of the surface of the gel, or that the gels can spill out of the container.

In order to avoid the above-mentioned problems, it has been proposed to enclose the gel compositions into vapor permeable bags or use mechanically stronger resins such as carrageerians or polyurethanes. However, none of the solutions is satisfactory as, on the one hand, the use of a bag does not prevent the gel from being deformed and changing its releasing properties and, on the other hand, the gels based on carrageenans or polyurethane resins, compared to the polyacrylate based gel, have inferior performance as a consequence of their tighter matrix. Moreover gels based on carrageenans need elevated processing temperatures, obviously a disadvantage when working with volatile compounds.

Therefore there is still a need for gel compositions which can be obtained at room temperature and are capable of having improved mechanical properties and still performing effective release of the active ingredient for a prolonged period of time.

SUMMARY OF THE INVENTION

We have now surprisingly discovered that, by using a super-absorbent polymer together with a suitable cross-linking agent, it is possible to obtain gel compositions associating an effective release of the active ingredient for a prolonged period of time and good mechanical properties. An additional advantage of these compositions is that they can be produced at room temperature.

Accordingly, the invention relates to a gel composition for improving air quality by releasing an active volatile therein over time. This composition comprises a water-based medium, an active volatile in an amount sufficient to provide perceptible or desirable benefits in the quality of the air into which the active volatile is released, a super-absorbent polyacrylate based polymer in an amount sufficient to form a gel, and a polymeric cross-linking agent having a molecular weight of between 10000 and 35000 g/mol and the ability to be polarized with positive charges, and being present in an amount sufficient to modify the mechanical properties of the gel.

The invention also relates to a consumer article of a dispenser for active volatiles comprising or associated with the compositions disclosed herein. A perfume dispenser is a preferred embodiment. In particular, dispensers for gel-type compositions are disclosed.

Finally, the invention relates to a method for improving air quality by releasing an active volatile therein over time, with the active volatile released from one of the compositions or dispensers disclosed herein.

DETAILED DESCRIPTION OF THE PREFERRED EMBODIMENTS

Figure 1:
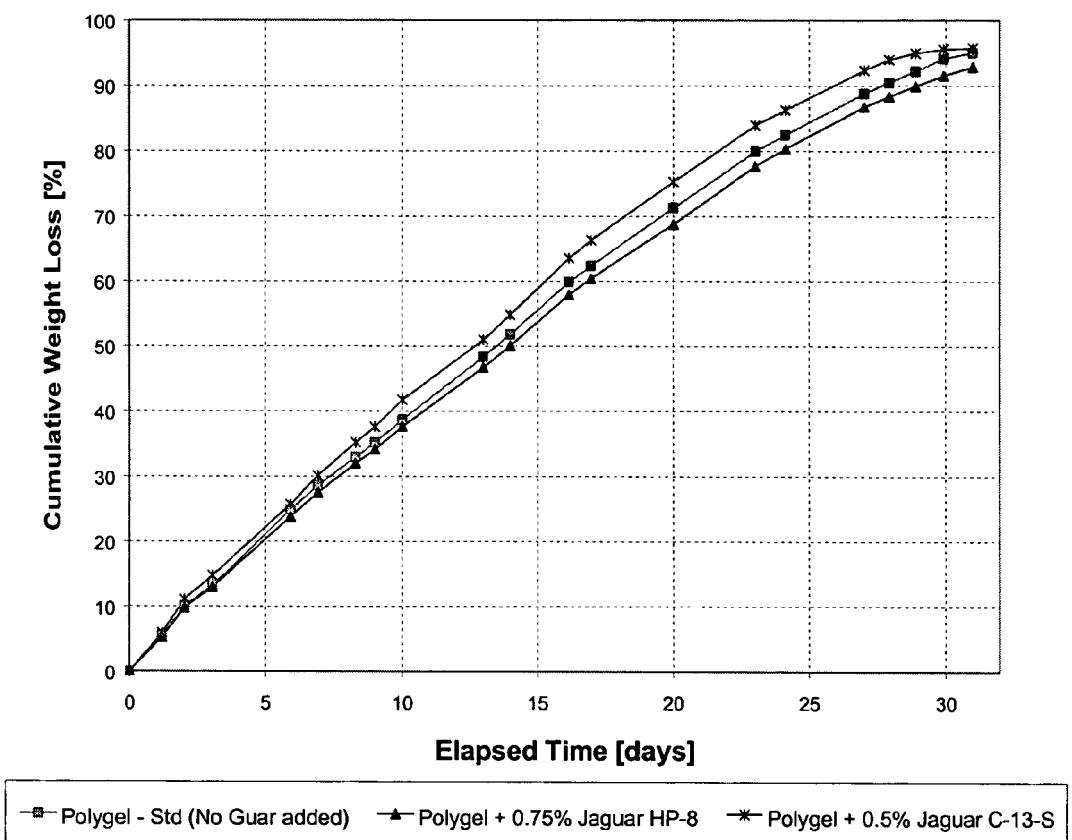
FIG. 1 is a graph of weight loss compared to time for various gel compositions.

The compositions according to the invention basically comprises:
a) a water based medium, comprising an active volatile;
b) a super-absorbent polyacrylate based polymer; and
c) a polymeric cross-linking agent having a high molecular weight and being able to be polarized with positive charges.

The water-based medium may be a solution, suspension or emulsion of the active volatile in a water based solvent. By "water based medium or solvent" we mean here preferably pure water, however it is possible use water containing a small amount of an alcohol such as a $C_2$ to $C_6$ alcohol. By the expression "small amount" we mean here approximately less than 10%, or even less than 5%, in respect of the total weight of the water based medium. More preferably, as water based medium will be used de-ionized water, or water with a content in salts below 0.5%, in respect to the weight of the water based medium.

Whenever the water-based medium is in the form of a solution, suspension or emulsion, the medium may advantageously comprise an emulsifying agent, although this is optional. Indeed, water-based medium have been prepared and found to function satisfactorily without the use of an emulsifying agent. However, when the emulsifying agent is used, e.g. for practical reasons, in general it will be a surfactant.

Where surfactants are used, non-ionic surfactants are preferred. Examples of this class of surfactants include ethoxylated sorbitan esters which are available under the trade names of SPAN® (origin: ICI) and BRIJ® (origin: ICI). Ethoxylated saturated fatty esters such as those sold under the names of CREMOPHOR® (origin: BASF) and LUTENSOL® (origin: BASF) can also be used. Further examples of appropriate non-ionic surfactants include alcohol ethoxylates, polyethylene glycol esters and ethylene oxide/propylene oxide copolymers.

As previously mentioned, the water based medium comprises an active volatile which will be diffused by the composition of the invention. The active volatile is preferably an organic oil capable of bringing a benefit into the surrounding air.

As active volatile, there can be used for example perfumes or perfuming ingredients, resulting thus in compositions particularly useful for the perfuming of a closed space, such as an air-freshener. Other suitable active volatiles comprise an insect repellent or attractant or a deodorizing or sanitizing agent, or yet any other volatile material capable of imparting perceptible and desirable benefits to the quality of the air into which it is diffused.

As a perfume or perfuming ingredient there can be used in the composition of the invention any ingredient or mixture of ingredients currently used in perfumery. The latter can be made of discreet chemicals; more often, however, it will be a more or less complex mixture of volatile ingredients of natural or synthetic origin. The nature of these ingredients can be found in specialized books of perfumery, e.g. in S. Arctander (Perfume and Flavor Chemicals, Montclair N.J., USA 1969) or similar textbooks of reference, and a more detailed description thereof is not warranted here.

Although special mention has been made hereinabove of the perfuming effect that can be exerted by the invention composition, the same principles apply to the manufacture of analogous compositions for the diffusion of deodorizing or sanitizing vapors, the perfume base being then replaced by a deodorizing composition, a bactericide, an insecticide, an insect repellent or even an insect attractant. By the term "sanitizing vapors", we refer here not only to the vapors of those substances which can enhance the degree of acceptance of surrounding air to the observer, but also to those substances which can exert an attractant or repellent effect towards certain species of insects, for instance towards houseflies or mosquitoes, or else, which can have bactericide or bacteriostatic activity. It goes without saying that mixtures of such agents can also be used.

Preferably, the active volatile will be a low polarity liquid. By "low polarity liquid" it is meant here a liquid containing less than 30%, in respect of the total weight of the active volatile, of polar ingredients, e.g. such as alcohols, glycol ethers, dipropylene glycol, propylene glycol or 3,6-dioxa-1-octanol.

More preferably the active volatile will be a low polarity perfume or perfume ingredient.

A person skilled in the art of preparing an active volatile, as hereinabove defined, will be perfectly able to choose the ingredients, as well as their concentrations, needed for the manufacture of a low polar active volatile capable of imparting the desired benefits.

The super-absorbent polyacrylate based polymer, intended to be mixed with the other constituents of the invention's composition, is a material or substance capable of absorbing large amounts of water or other water based media. In the context of the present invention, the material is a synthetic polymer containing acrylic acid or methacrylic acid, or a salt thereof. The super-absorbent polyacrylate based polymer is thus capable of absorbing between about 10 to 200 times, preferably between 50 and 200 times, its own weight of water or hydrophilic solvent.

Examples of useful super-absorbent polyacrylate based polymers are polymers of acrylic acid or methacrylic acid or salts thereof, cross-linked polymers of the acrylic acid or methacrylic acid or a salt thereof, partially saponified polyacrylamides, partially saponified polyacrylic or polymethacrylic esters, partially saponified graft polymers of acrylonitrile, graft polymers of starch and acrylic acid or a salt thereof or copolymers of acrylates, methacrylates, acrylic acid, methacrylic acid or a salt thereof with vinyl acetate, vinyl alcohol or maleic anhydride.

A preferred super-absorbent material is a cross-linked polyacrylic or methacrylic acid or a salt thereof.

Even more preferred is a cross-linked sodium polyacrylate/polyacrylic acid polymer. Superabsorbents of this type are commercially available under the names of SALSORB® (Ciba Speciality Chemicals) and CABLOC® (Stockhausen GmbH).

The superabsorbents of the invention, which are in the form of fine powders, have preferably a particle size below 500 microns, more preferably from about 50 to about 500 microns, in order to provide smooth gels upon admixture of the components. Powders with larger particle sizes than those mentioned could also be used, but they will result in coarser gels with longer gelling times.

The polymeric cross-linking agent plays an important role in the mechanical and release properties of the final composition. Suitable cross-linker agents for the purpose of the invention are polymers which have a sufficiently high molecular weight, and are able to be polarized with positive charges. By a polymer having a "high molecular weight" it is meant here a polymer having a molecular weight comprised between 10,000 g/mol and 350,000 g/mol.

It is important that the cross-linking agent does not have a too low molecular weight, otherwise the gel thus obtained will have a structure which is too tight and the benefits derived from the super-absorbent polyacrylate based polymers will be partially lost. By using a cross-linking polymer such as defined hereinabove it is possible to retain all the advantages of a super-absorbent polyacrylate based polymer and impart the desired mechanical properties to the final gel. It is also understood that by modulating the molecular weight of the cross-linking agent it is possible to tune the mechanical behavior of the invention's gel composition.

The ability to be polarized with positive charges is also an important aspect of the cross-linking agent. By the expression "ability to be polarized with positive charges" we mean here that the cross-linking agent possesses groups having either one or more permanent positive charges or the ability to bear one or more positive charges, e.g. by protonation of neutral functional groups. Indeed, the reticulating interactions between the polyacrylate based polymer, which can bear negative charges, and the cross-linking agent are believed to be grounded on an electrostatic effect.

Amongst the different available polymers which can satisfy the above-mentioned criteria, one can cite, as non limiting examples, cross-linking agents such as a polyalkylamine, a cationic polyacrylamide, a guar-gum or their derivatives. The cross-linking agents may be linear or branched with side chains, the latter may also be derivatized.

Examples of polyamines and cationic polyacrylamides, as well as derivatives thereof, which are useful for the purpose of the invention are the compounds known under the trademark AGEFLOC® (origin: Ciba Specialty Chemicals, Switzerland) or the trademark POLYMIN® (origin: BASF, Germany). A dimethylamine/epichlorohydrin co-polymer, such as the one known as AGEFLOC® B50, represents a more specific example of polyalkylamine.

The guar-gums or a derivative thereof, which represent the preferred class of cross-linking agents, are hydrocolloidal polysaccharides which can be obtained from the guar plant. In general, the gums are based on a mannose backbone, and galactose side chains, with a mannose/galactose ratio ranging between 2/1 to 4/1. Suitable derivatives of the guar-gum may be those which have been derivatized with hydroxy alkyl groups which may contain ammonium or sulfonium halide groups. Examples of such derivatizing groups are the following:

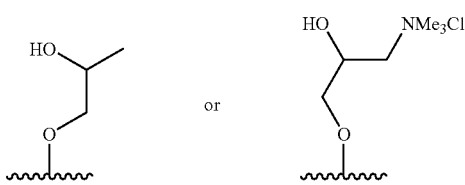

Examples of guar-gums and derivatives thereof and are the compounds known under the trademark JAGUAR® (origin: Rhodia, France) and some of them are mentioned in EP 934343.

Preferably, the cross-linking agent will be a derivatized guar-gum with a molecular weight comprised between 100,000 g/mol and 300,000 g/mol, the guar-gum being derivatized with hydroxy $C_2$ to $C_6$ alkyl groups possibly containing a $C_3$ to $C_{20}$ ammonium halide, and the degree of substitution of the polymers being comprised between 0.01 and 1.2. The expression "degree of substitution" refers to the average number of moles of derivatizing groups per anhydro-sugar unit in the gum. An example of such compounds is the one having the CAS Number 39421-75-5, or 2-hydroxypropyl guar-gum ether, also known under the trademark JAGUAR®, grades HP 8.

Amongst the above-mentioned derivatized guar-gum, one may cite in particular the ones derivatized with 2-hydroxypropyl-3-(trimethylammoniumchloride) groups and possibly 2-hydroxypropyl groups, and the degree of substitution of the polymers being comprised between 0.1 to 0.25. An example of such compounds are the ones having the CAS Number 65497-29-2, or 2-hydroxypropyl-3-(trimethylammoniumchloride) guar-gum ether, also known under the trademark JAGUAR®, grades C-13-S or C 17.

The above-identified constituents of the composition can be admixed in various ratios depending on the nature of the different constituents.

One can cite, as non-limiting examples and for all types of consumer articles associated with the composition, compositions wherein: a) the active volatile is present in an amount comprised between 0.01% and 30%; b) the super-absorbent polyacrylate based polymer is present in an amount comprised between 0.2% and 5%; c) the cross-linking agent is present in an amount comprised between 0.01% and 5%; d) the surfactant is present in an amount comprised between 0% and 5%; e) the alcohol is present in an amount comprised between 0% and 5% and water constitutes the balance of the composition, the percentages above being relative to the weight of the composition.

Preferably, one can cite compositions wherein: a) the active volatile is present in an amount comprised between 3% and 6%; b) the super-absorbent polyacrylate based polymer is present in an amount comprised between 1% and 2%; c) the cross-linking agent is present in an amount comprised between 0.1% and 1.5%; d) the surfactant is present in an amount comprised between 0% and 1%; e) the alcohol is present in an amount comprised between 0% and 2% and water constitutes the balance of the composition, the percentage being relative to the weight of the composition.

Naturally, it is clear to a person skilled in the art that the various components can be admixed in any amount required to optimize the performance of the invention's compositions.

The invention's composition may further comprise additional and optional components that can have a beneficial effect on the final composition. The optional components may be a preservative, an antioxidant or an indicator which helps the consumer to assert when the active volatile is no more present in the composition, i.e. an end point indicator. The total amount of the optional ingredients may be comprised between 0% and 5%, preferably between 0.01% and 0.5%, the percentage being relative to the weight of the composition.

One of the optional components is silica, and more specifically fumed silica. Silica can be incorporated into the invention's composition as end point indicator and also to slightly improve the structure of the gel or composition according to the invention. Suitable kinds of silica are known under the tradename AEROSIL® (from Degussa, Germany) or CABOSIL® (from Eager Plastics Inc.)

As anticipated above, the composition of the invention can be contained in, or associated with, a consumer article, whereby as a consumer article it is intended here more specifically a volatile material dispenser. Therefore, a consumer article in the form of a volatile material dispenser containing, or associated with, an invention's composition is also an object of the present invention.

Such a volatile material dispenser can be, depending on the nature of the active volatile used in the preparation of the composition, a perfuming or sanitizing device. Non-limiting examples of the volatile material dispenser are an air-freshener, particularly of the solid type, a diaper pail freshener, a car freshener, a closet freshener, a wardrobe air-freshener, a drawer freshener, a cat litter box freshener, a shoe freshener or a garbage pail freshener, an insecticide or an insect repellent device.

The preferred consumer article is an air-freshener of the gel type.

In fact, a container and an adequate composition of the invention will compose the consumer article. The composition will be housed by the container and at least a portion of the container surface is able to allow the release of the vapors of the volatile liquid component into the air surrounding the consumer article. The container can be made of any material usable for this kind of consumer article. Naturally the material must be chemically inert towards the composition of the invention. Standard packages used for these kinds of articles, such as plastics-polypropylene, polyvinyl chloride, high density polyethylene, P.E.T. and glass, are well suited.

During storage, at least the portion of the container that is able to allow the release of the vapors into the exterior of the contained is sealed, in order not to allow diffusion of the volatile liquid phase into the surroundings. The consumer will then activate the consumer article simply by removing the seal, after which the volatile liquid phase will start to diffuse into the surrounding air.

EXAMPLE

The invention will now be described in further detail by way of the following examples.

Example 1

Examples of Compositions for a Solid Air-freshener

Perfuming compositions were prepared by admixing the following ingredients, in a variety of proportions within the ranges indicated:

| Ingredients | Range of concentrations % by weight |
| --- | --- |
| Benzyl Acetate | 20–30 |
| Linalyl Acetate | 15–25 |
| Isobornyl acetate | 5–20 |
| DIPG Monomethyl ether | 10–20 |
| Dipropylene Glycol | 5–10 |
| Terpineol | 1–5 |
| Eucalyptus oil | 0.2–3 |
| Methyl nonyl aldehyde | 0.2–3 |
| Dihydromyrcenol | 10–20 |
| Terpinyl acetate | 0.5–5 |

By using anyone of the perfumes thus obtained, perfuming compositions according to the invention, or air-fresheners, were prepared with the following ingredients, in the proportions indicated:

Composition (A)

An air-freshener composition was prepared by mixing the following ingredients in the indicated amounts:

| Ingredients | Parts by weight |
| --- | --- |
| De-ionized water | 95.5 |
| JAGUAR ® C-13-S[1] | 0.5 |
| CABLOC ® CT[2] | 1.0 |
| Perfuming composition | 3.0 |

[1] derivatized guar gum; origin: Rhodia
[2] super-absorbent sodium polyacrylate based resin; origin: Stockhausen GmbH Composition (B)

An air-freshener composition was prepared by mixing the following ingredients in the indicated amounts:

| Ingredients | Parts by weight |
| --- | --- |
| De-ionized water | 95.25 |
| JAGUAR ® HP8[1] | 0.75 |
| SALSORB ®[2] | 1.00 |
| Perfuming composition[1] | 3.00 |

[1] as for composition (A)
[2] super-absorbent sodium polyacrylate based resin; origin: Ciba Speciality Chemicals General Procedure of the Preparation of the Perfuming Composition and the Resulting Air-freshener Operating at room temperature, the JAGUAR® polymer was added to the water and mixed thoroughly until hydrated. To this mixture, and under stirring was then added the perfume composition. Finally, the sodium polyacrylate was added to the water solution which was quickly stirred and poured into a mould or container. The composition according to the invention thus obtained was set within approximately 30 seconds in a gel having good mechanical properties and thus being able to stand alone with minimal deformation, unlike the prior art polyacrylate based composition which has the typical mechanical properties of an agglomerate of separate swollen particles.

Results of the Release Test

FIG. 1 is aimed to illustrate that the gel compositions according to the invention, despite their improved mechanical properties if compared to a prior art polyacrylate compositions, are able to perform an effective release of the active volatile for a prolonged period of time. It is remarkable that the cross-linked gels of the invention have release performances at least as good as the prior art polyacrylate compositions.

What is claimed is:

1. A gel composition for diffusing an active volatile, obtainable by admixing of:
   a) an active volatile in an amount of between 0.01 and 30% by weight;
   b) a super-absorbent polyacrylate based polymer in an amount of between 0.2 and 5% by weight;
   c) a polymeric cross-linking agent comprising a polyalkylamine, a cationic polyacrylamide, a guar-gum, or a guar-gum derivatized with a hydroxy bearing $C_2$ to $C_6$ alkyl group, the agent having a molecular weight of between 10000 g/mol and 350000 g/mol and being present in an amount of between 0.01 and 5% by weight;
   d) an emulsifying agent in an amount of between 0 and 5% by weight;
   e) an alcohol in an amount of between 0 and 5% by weight;
   all percentages being relative to the total weight of the composition, with the balance being substantially formed of water.

2. A gel composition according to claim 1, wherein the active volatile ingredient is present in an amount comprised between 3 and 6% by weight, component b) is present in an amount comprised between 1 and 2% by weight, component c) is present in an amount comprised between 0.1 and 1.5% by weight, component e) is present in an amount comprised between 0 and 1% by weight and component e) is present in an amount comprised between 0 and 2%.

3. A gel composition according to claim 1, comprising an emulsifying agent.

4. A gel composition according to claim 1, which is free of alcohol.

5. A gel composition according to claim 4, wherein the water is de-ionised water, or water having a content in salts below 0.5% by weight.

6. A gel composition according to claim 1, wherein said active volatile is a perfume, a perfuming ingredient, a deodorizing composition, a bactericide, an insecticide or an insect repellent or attractant.

7. A gel composition according to claim 6, wherein said active volatile is a perfume or a perfuming ingredient containing less than 30% by weight of polar ingredients, in respect to the total weight of said active volatile.

8. A gel composition according to claim 1, wherein said super-absorbent polyacrylate based polymer is a polymer of acrylic acid or methacrylic acid or a salt thereof, cross-linked polymers of the acrylic acid or methacrylic acid or a salt thereof, partially saponified polyacrylamides, partially saponified polyacrylic or polymethacrylic esters, partially saponified graft polymers of acrylonitrile, graft polymers of starch and acrylic acid or a salt thereof or copolymers of acrylates, methacrylates, acrylic acid, methacrylic or a salt thereof acid with vinyl acetate, vinyl alcohol or maleic anhydride.

9. A gel composition according to claim 8, wherein said super-absorbent polyacrylate based polymer is a cross-linked polyacrylic or methacrylic acid or a salt thereof.

10. A gel composition according to claim 9, wherein said super-absorbent polyacrylate based polymer is a cross-linked sodium polyacrylate/polyacrylic acid polymer.

11. A gel composition according to claim 1, wherein said polymeric cross-linking agent is a polyalkylamine or a cationic polyacrylamide.

12. A gel composition according to claim 11, wherein said polymeric cross-linking agent is a guar-gum derivatized with a hydroxy bearing $C_2$ to $C_6$ alkyl group.

13. A gel composition according to claim 1, wherein said polymeric cross-linking agent is a derivatized guar-gum having a molecular weight of between 100000 g/mol and 300000 g/mol, said guar-gum being derivatized with hydroxy $C_2$ to $C_6$ alkyl groups optionally containing a $C_3$ to $C_{20}$ ammonium halide, and with a degree of substitution of the polymers being between 0.01 and 1.2.

14. A gel composition according to claim 13, wherein said derivatized guar-gum is derivatized with 2-hydroxypropyl-3-(trimethylammoniumchloride) groups and possibly 2-hydroxypropyl groups, and the degree of substitution of the polymers being comprised between 0.1 to 0.25.

15. A gel composition according to claim 13, wherein the super-absorbent polyacrylate based polymer is a cross-linked polyacrylic or methacrylic acid or a salt thereof, and preferably a cross-linked sodium polyacrylate/polyacrylic acid polymer.

16. A gel composition according to claim 1, which further comprises silica.

17. A consumer article in the form of a volatile material dispenser article comprising a gel composition obtainable by admixing of:

a) an active volatile in an amount of between 0.01 and 30% by weight;

b) a super-absorbent polyacrylate based polymer in an amount of between 0.2 and 5% by weight;

c) a polymeric cross-linking agent comprising a polyalkylamine, a cationic polyacrylamide, a guar-gum or a guar-gum derivatized with a hydroxy bearing $C_2$ to $C_6$ alkyl group, the agent having a molecular weight of between 10000 g/mol and 350000 g/mol and being present in an amount of between 0.01 and 5% by weight;

d) an emulsifying agent in an amount of between 0 and 5% by weight;

e) an alcohol in an amount of between 0 and 5% by weight;

all percentages being relative to the total weight of the composition, with the balance being substantially formed of water.

18. A volatile material dispenser according to claim 17, in the form of an air-freshener, a diaper pail freshener, a car freshener, a closet freshener, a wardrobe air-freshener, a drawer freshener, a cat litter box freshener, a shoes freshener, a garbage pail freshener or an insecticide or an insect repellent device.

19. A volatile material dispenser according to claim 17, in the form of an air-freshener of the gel type.

* * * * *